United States Patent [19]

Sanderson et al.

[11] Patent Number: 4,554,364
[45] Date of Patent: Nov. 19, 1985

[54] PRODUCTION OF 2-HYDROXYALKYL-1,3-DIOXOLANES

[75] Inventors: John R. Sanderson; Ernest L. Yeakey, both of Austin; Jiang-Jen Lin, Round Rock, all of Tex.

[73] Assignee: Texaco Inc., White Plains, N.Y.

[21] Appl. No.: 683,547

[22] Filed: Dec. 19, 1984

[51] Int. Cl.$^4$ .......................................... C07D 317/00
[52] U.S. Cl. .................................................. 549/453
[58] Field of Search .......................................... 549/453

[56] References Cited

U.S. PATENT DOCUMENTS

| | | | |
|---|---|---|---|
| 2,140,938 | 12/1938 | McNamee et al. | 549/453 |
| 2,862,978 | 12/1958 | Skinner et al. | 549/453 |
| 4,200,765 | 4/1980 | Goetz | 549/449 |
| 4,337,371 | 6/1982 | Kollar | 568/852 |

FOREIGN PATENT DOCUMENTS

| | | | |
|---|---|---|---|
| 1957621 | 5/1971 | Fed. Rep. of Germany | 549/453 |
| 488327 | 7/1938 | United Kingdom | 549/453 |

*Primary Examiner*—Ethel G. Love
*Attorney, Agent, or Firm*—Jack H. Park; Kenneth R. Priem

[57] ABSTRACT

It has been surprisingly discovered in accordance with the present invention that when 1,3-dioxolane is reacted with formaldehyde in the presence of tert-butyl hydroperoxide and a cobalt initiator, the reaction preferentially involves an addition of the formaldehyde to the 2-methylene group of the 1,3-dioxolane with only minor reaction with the 4-methylene and 5-methylene groups of the 1,3-dioxolane whereby the reaction product that is formed contains significant quantities of 2-hydroxyalkyl-1,3-dioxolanes and only minimal amounts of the undesired methyl formate by-product. 2-Hydroxymethyl-1,3-dioxolane is hydrolyzed with comparative ease to ethylene glycol and the corresponding glycol aldehyde ($CHO-CH_2-OH$). The glycol aldehyde in turn can be catalytically hydrogenated to form additional quantities of ethylene glycol.

6 Claims, No Drawings

PRODUCTION OF 2-HYDROXYALKYL-1,3-DIOXOLANES

BACKGROUND OF THE INVENTION

1. Technical Field of the Invention

This invention relates to the manufacture of 2-hydroxyalkyl-1,3-dioxolanes. More particularly, this invention relates to a method wherein 1,3-dioxolane is reacted with formaldehyde in the presence of t-butyl hydroperoxide and a cobalt compound to provide 2-hydroxyalkyl-1,3-dioxolanes. The 2-hydroxyalkyl-1,3-dioxolanes are useful as raw materials for the manufacture of ethylene glycol.

2. Prior Art

Kollar U.S. Pat. No. 4,337,371 discloses a method for the preparation of ethylene glycol wherein methanol and formaldehyde are reacted in the presence of an organic peroxide and water to provide ethylene glycol. In a technical article Oyama discloses the free-radical reaction of primary and secondary alcohols such as methanol, 2-propanol, ethanol, 2-butanol and 3-methyl-2-butanol with formaldehyde, and t-butyl peroxide to provide glycols (*J. Org. Chem.*, 30, 2429 (1965). Watanabe et al. in an article in *Bull. Chem. Soc.Jpn.*, 56, 1428-1430 (1983), Vol. 56, No. 5 disclose the reaction of 1,3-dioxolane with electron-deficient alkenes such as diethyl maleate, maleic anhydride, etc. Russian Author's Certificate No. 975,704 (Imashev et al.) discloses a method wherein 1,3-dioxolane is oxidized with molecular oxygen at a temperature of about 10° to 60° C. to provide ethylene glycol monoformate as a principle reaction product.

Related Copending Patent Applications

Copending coassigned Sanderson et al. U.S. patent application Ser. No. 683,549, filed Dec. 19, 1984 (filed of an even date herewith) discloses a method wherein 1,3-dioxolane is oxidized to provide the corresponding hydroperoxide which, in turn, is used to catalyze the reaction of additional quantities of 1,3-dioxolane with formaldehyde to provide 2-hydroxymethyl-1,3-dioxolane.

Copending coassigned Sanderson et al. U.S. patent application Ser. No. 683,441, filed Dec. 19, 1984 (filed of an even date herewith) discloses a method wherein 2-hydroxymethyl-1,3-dioxolane is prepared by the reaction of 1,3-dioxolane with formaldehyde in the presence of an organic peroxide under non-acidic conditions.

Copending coassigned Yeakey et al. U.S. patent application Ser. No. 683,546, filed Dec. 19, 1984 (of an even date herewith), discloses a method wherein dimethoxymethane is reacted with paraformaldehyde in the presence of an organic peroxide to provide an ethylene glycol precursor.

SUMMARY OF THE INVENTION

It has been surprisingly discovered in accordance with the present invention that when 1,3-dioxolane is reacted with formaldehyde in the presence of t-butyl hydroperoxide and a cobalt initiator, the reaction preferentially involves an addition of the formaldehyde to the 2-methylene group of the 1,3-dioxolane with only minor reaction with the 4-methylene and 5-methylene groups of the 1,3-dioxolane whereby the reaction product that is formed contains significant quantities of 2-hydroxyalkyl-1,3-dioxolanes. The 2-hydroxyalkyl-1,3dioxolanes are hydrolyzed with comparative ease to ethylene glycol and the corresponding glycol aldehyde (CHO-CH$_2$-OH). the glycol aldehyde in turn can be catalytically hydrogenated to form additional quantities of ethylene glycol.

DETAILED DESCRIPTION OF THE INVENTION

Starting Materials

The starting materials for the present invention are 1,3-dioxolane, formaldehyde t-butyl hydroperoxide and a cobalt compound.

Formaldehyde may be employed in its conventional form, as an aqueous formaline solution, in "inhibited" methanol solution, such as paraformaldehyde, or trioxane. Formalin is a preferred starting material.

The organic peroxide employed in the process of the present invention is t-butyl hydroperoxide.

The cobalt compound to be used is suitably an at least partially soluble salt of an organic carboxylic acid, such as an organo-metallic salt of cobalt (e.g., cobalt acetate, cobalt naphthanate, cobalt acetylacetonate, etc.).

Reaction Conditions

The desired products of the present invention, 2-hydroxyalkyl-1,3-dioxolanes, are addition products of formaldehyde and 1,3-dioxolane. They may be represented graphically by the following formulae:

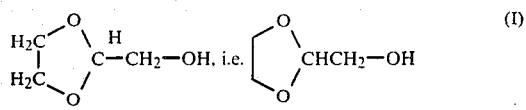

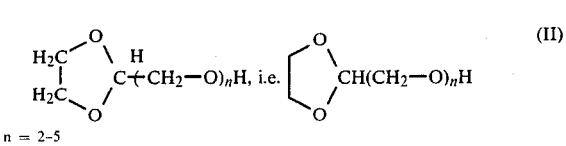

n = 2-5

A molar excess of either of the reactants may be used, if desired. Formaldehyde may be used in a molar excess (e.g., from about 1 to about 5 moles of formaldehyde per mole of 1,3-dioxolane.

The t-butyl hydroperoxide is suitably used in an amount ranging from about 0.01 to about 10 wt. %, based on the 1,3-dioxolane. More preferably, from about 2 to about 5 wt. % of t-butyl hydroperoxide is used. Only a minor amount of the cobalt compound is required and satisfactory results are obtainable using as little as about 0.0001 wt. % of the cobalt compound, based on the 1,3-dioxolane. Larger amounts up to about 5 wt. %, based on the 1,3-dioxolane, may be used, but there is no particular advantage in using more than about 5 wt. % of the cobalt compound.

The reaction is suitably conducted at a temperature within the range of about 80° to about 250° C., and more preferably, within the range of about 80° to about 150° C.

The reaction is preferably conducted at atmospheric pressure. Superatmospheric or subatmospheric pressures may be used if desired, but there is no particular advantage in doing so.

Reaction times of from about 0.5 to about 10 hours may be employed with satisfactory results. More preferably, the reaction time will be within the range of about 1 to about 5 hours.

The reaction can be conducted in inert solvent solution with a solvent such as acetonitrile, t-butyl alcohol, monochlorobenzene, benzene, etc. but there is no particular advantage in doing so.

At the end of the reaction, the reaction mixture may be separated into components by any suitable technique such as filtration, distillation, solvent extraction, etc.

As indicated earlier, the 2-hydroxyalkyl-1,3-dioxolanes can be hydrolyzed to provide ethylene glycol and glycolaldehyde under conditions as disclosed, for example in J. D. Roberts, M. C. Caserio, "Basic Principles of Organic Chemistry", W. A. Benjamin, Inc., New York, 1965. See page 443. The glycolaldehyde may also be catalytically hydrogenated to form additional quantities of ethylene glycol under conditions of the type disclosed by H. O. Hause, "Modern Synthetic Reactions", 2nd Ed., W. A. Benjamin, Inc., 1972. See Chapter 1 and references therein.

SPECIFIC EXAMPLES

EXAMPLE 1

1,3-Dioxolane (80 ml), paraformaldehyde (10 g) and tert-butyl hydroperoxide (3.00 ml) were charged to a 300 cc. stainless steel autoclave equipped with a magne drive stirrer. The autoclave was heated slowly (over one hour) to the desired temperature and held at this temperature for the desired time. The autoclave was cooled to ambient temperature and the solid paraformaldehyde filtered from the reaction mixture. The reaction conditions are shown in Table I.

TABLE I 1,3-DIOXOLANE WITH FORMALDEHYDE

| Notebook Number | Time (Hr) | Temp (°C.) | Ethanol | Ethyl Formate | Glycol Ether Acetates | $\begin{array}{c}O\\ \diagdown\\ CHCH_2-OH\\ \diagup\\ O\end{array}$ | $\begin{array}{c}O\\ \diagdown\\ CH(CH_2-O)_n-H^d\\ \diagup\\ O\end{array}$ |
|---|---|---|---|---|---|---|---|
| 5807-85 | 2 | 180 | 4.14 | 16.60 | 1.44 | 8.98 | 3.85 |
| 5807-84 | 3 | 160 | 3.39 | 17.52 | 1.67 | 9.97 | 4.24 |
| 5807-83 | 5 | 140 | 1.46 | 16.16 | 2.09 | 12.10 | 4.07 |
| 5807-48 | 2 | 130 | — | — | — | — | — |
|  | 2 | 140 | 1.48 | 12.11 | 2.17 | 13.94 | 5.06 |

$^c$ = Products determined on sample after solid paraformaldehyde had been removed.
$^d$ = n = 2-5

As will be seen from Table I, good yields of 2-hydroxymethyl-1,3-dioxolane were obtained in all of the runs.

EXAMPLE 2

Procedure

A 250 ml flask equipped with water-cooled condenser, magnetic stirrer, heating mantle, thermometer (Therm-O-Watch), and dropping funnel was charged with 50 ml 1,3-dioxolane, 10 g paraformaldehyde and additive. The mixture was heated to a gentle reflux and a TBHP/dioxolane mixture added over several hours. [The TBHP/dioxolane mixture was prepared by adding 3.00 ml 65% TBHP/TBA to 30 ml 1,3-dioxolane]. At the end of the reaction, the mixture was cooled to ambient temperature and the solid paraformaldehyde filtered off. The products were determined by GC. The results are summarized in the following Tables II and III. A comparison example is included.

TABLE II

Reaction of 1,3-Dioxolane with Formaldehyde

| Notebook Number | 1,3-Dioxolane (ml) | Paraformaldehyde (g) | TBHP$^a$ (ml 65%) | Additive | Time (Hr) | Temp (°C.) |
|---|---|---|---|---|---|---|
| 5831-6 | 50 (+30) | 10.0 | 3.00 | cobalt octate (5 d) | 7 | 75 |
| 5831-10 | 50 (+30) | 10.0 | 3.00 | Fe complex (0.05 g) | 6 | 75 |
| 5831-12 | 50 (+30) | 10.0 | 3.00 | cobalt octate (10 d) | 7 | 75 |
| 5831-22 | 50 (+30) | 10.0 | 3.00 | Fe(AcAc)₃ (0.05) | 5 | 75 |
| 5831-24 | 50 (+30) | 10.0 | 3.00$^d$ | cobalt octate (10 d) | 8 | 75 |
| 5831-25 | 50 (+30) | 10.0 | 3.00 | chromium acetate (0.05 g) | 7 | 75 |
| 5831-27 | 50 (+30) | 10.0 | 6.00 | cobalt octate (10 d) | 7 | 75 |
| 5807-83$^c$ | 80.0 | 10.0 | DTBP 3.00 | — | 5 | 140 |

TABLE III

Reaction of 1,3-Dioxolane with Formaldehyde

Products, (Area %)

| Notebook | TBA | Ethyl Formate | Glycol Ether Acetates | 2-Hydroxy-methyl-1,3-dioxolane | $\begin{array}{c}O\\ \diagdown\\ CH(CH_2-O)_n-H^c\\ \diagup\\ O\end{array}$ |
|---|---|---|---|---|---|
| 5831-6 | 3.16 | Trace | 1.69 | 4.08 | 0.94 |
| 5831-10 | 3.39 | sh$^b$ | 1.67 | 2.72 | 1.50 |
| 5831-12 | 3.13 | 0.64 | 1.54 | 9.60 | 1.66 |
| 5831-22 | 3.42 | — | 0.86 | 0.38 | — |
| 5831-24 | 3.04 | 0.41 | 1.64 | 4.04 | 0.64 |
| 5831-25 | 2.23 | 0.28 | 0.58 | 2.76 | 0.43 |
| 5831-27 | 4.66 | 0.76 | 2.27 | 6.18 | 1.28 |

TABLE III-continued

Reaction of 1,3-Dioxolane with Formaldehyde

| | | | Products, (Area %) | | |
|---|---|---|---|---|---|
| Notebook | TBA | Ethyl Formate | Glycol Ether Acetates | 2-Hydroxy-methyl-1,3-dioxolane | 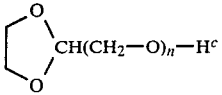 |
| 5807-83[e] | 5.05 | 16.16 | 2.09 | 12.10 | 4.07 |

[a] = TBHP = tert-butylhydroperoxide; DTBP = di-tert-butylperoxide
[b] = shoulder on tert-butylalcohol peak
[c] = n = 2-5
[d] = added all at once
[e] = reaction conducted in 300 cc stainless steel autoclave Note from Tables II and III that the formation of ethyl formate by-products was virtually eliminated when the reaction was catalyzed with tert-butyl hydroperoxide promoted with cobalt octate. In contrast, the results from 5807-83 show that the yield of ethyl formate was significant.

The foregoing examples are given by way of illustration and are not intended as limitations on the scope of the present invention, which is defined by the appended claims.

What is claimed is:

1. A method for the preparation of 2-hydroxyalkyl-1,3-dioxolanes which comprises reacting 1,3-dioxolane with formaldehyde and a cobalt compound in the presence of tert-butyl hydroperoxide.

2. A method as in claim 1, wherein the cobalt compound is an at least partially soluble cobalt salt of an organic carboxylic acid.

3. A method as in claim 2, wherein the cobalt compound is cobalt octoate.

4. A method which comprises the steps of reacting 1,3-dioxolane with from about 0.5 to about 5 moles of formaldehyde per mole of dioxolane at a temperature within the range of about 80° to about 250° C. in the presence of from about 0.01 to about 10 wt. % of tert-butylhydroperoxide and 0.0001 to 5 wt. % of a cobalt compound, based on the 1,3-dioxolane and recovering 2-hydroxyalkyl-1,3-dioxolanes from the products of the reaction.

5. A method as in claim 4, wherein the cobalt compound is an at least partially soluble cobalt salt of an organic carboxylic acid.

6. A method as in claim 3, wherein the cobalt compound is cobalt octoate.

* * * * *